US006083907A

United States Patent [19]
Uchida et al.

[11] Patent Number: 6,083,907
[45] Date of Patent: Jul. 4, 2000

[54] TREATMENT OF PEPTIC ULCERS USING MIDKINE (MK) PROTEINS

[75] Inventors: Masayuki Uchida; Shinya Ikematsu; Minehiko Yokoyama; Akio Yamashita; Hideshi Kumai; Munehiro Oda; Naoki Kato; Sadatoshi Sakuma; Takashi Muramatsu, all of Kanagawa, Japan

[73] Assignee: Meiji Milk Products Co., Ltd., Tokyo, Japan

[21] Appl. No.: 09/012,084

[22] Filed: Jan. 22, 1998

[51] Int. Cl.⁷ ..................................................... A61K 38/18
[52] U.S. Cl. ................................................ 514/2; 424/85.1
[58] Field of Search ................................. 514/2; 424/85.1

[56] References Cited

U.S. PATENT DOCUMENTS 5,210,026   5/1993   Kovesdi et al. .

OTHER PUBLICATIONS

Robson et al. (1992) Lancet 339(8784): 23–25, 1992.
Maekawa et al. (1999) J. Lab. Clin. Med. 133(4): 349–352, 1999.
JAPIO database on Dialog, acc. no. 05480654, citing JP published application no. 9095454, Apr. 1997.
Yoshida, Y. et al. (1995) "Midkine is present in the early stage of cereba infarct." Development Brain Research 85: 25–30.
Fabri, L. et al. (1992) "Characterization of Bovine Heparin–Binding Neurotrophic Factor (HBNF): Assignment of Disulfide Bonds." Biochemistry International 28(1): 1–9.
Kadomatsu, K. et al. (1988) "cDNA Cloning and Sequencing of a New Gene Intensely Expressed in Early Differentiation Stages of Embryonal Carcinoma Cells and in Mid–Gestation Period of Mouse Embryogenesis." Biochem. Biophys. Res. Commun. 151(3): 1312–1318.
Kojima, S. et al. (1995) "Midkine Enhances Fibrinolytic Activity of Bovine Endothelial Cells." J. Biol. Chem. 270(16): 9590–9596.
Kovesdi, I. et al. (1990) "Heparin–Binding Neurotrophic Factor (HBNF) and MK, Members of a New Family of Homologous, Developmentally Regulated Proteins." Biochem. Biophys. Res. Commun. 172(2): 850–854.
Li, Y–S. et al. (1990) "Cloning and Expression of a Developmentally Regulated Protein that Induces Mitogenic and Neurite Outgrowth Activity." Science 250: 1690–1694.
Merenmies, J. et al. (1990) "Molecular Cloning of the 18–kDa Growth–associated Protein of Developing Brain." J. Biol. Chem. 265(28): 16721–16724.
Muramatsu, H. et al. (1991) "Purification of Recombinant Midkine and Examination of Its Biological Activities: Functional Comparison of New Heparin Binding Factors." Biochem. Biophys. Res. Commun. 177(2): 652–658.
Muramatsu, H. et al. (1993) "Midkine, A Retinoic Acid–Inducible Growth/Differentiation Factor: Immunochemical Evidence for the Function and Distribution." Developmental Biology 159: 392–402.
Muramatsu, T. (1994) "The Midkine Family of Growth/Differentiation Factors." Develop. Growth & Differ. 36(1): 1–8.
Kojima, S. et al. (1995) "Synthetic Peptides Derived From Midkine Enhance Plasminogen Activator Activity in Bovine Aortic Endothelial Cells." Biochem. Biophys. Res. Commun. 206(2): 468–473.
Rauvala, H. (1989) "An 18–kd heparin–binding protein of developing brain that is distinct from fibroblast growth factors." The EMBO Journal 8(10): 2933–2941.
Tezuka, K. et al. (1990) "Isolation of Mouse and Human cDNA Clones Encoding a Protein Expressed Specifically in Osteoblasts and Brain Tissues." Biochem. Biophys. Res. Commun. 173(1): 246–251.
Tomomura, M. et al. (1990) "A Retinoic Acid–responsive Gene, MK, Found in the Teratocarcinoma System." J. Biol. Chem. 265(18): 10765–10770.
Tsutsui, J. et al. (1991) "A New Family of Heparin–Binding Factors: Strong Conservation of Midkine (MK) Sequences Between the Human and the Mouse." Biochem. Biophys. Res. Commun. 176(2): 792–797.
Tsutsui, J. et al. (1993) "A New Family of Heparin–binding Growth/Differentiation Factors: Increased Midkine Expression in Wilms' Tumor and Other Human Carcinomas." Cancer Research. 53: 1281–1285.
Unoki, K. et al. (1994) "Rescue of Photoreceptors From the Damaging Effects of Constant Light by Midkine, a Retinoic Acid–Responsive Gene Product." Invest. Ophthalmol. Vis. Sci. 35(12): 4063–4068.
Yamada, H. et al. (1997) "Simulation of collagen expression and glycosaminoglycan synthesis by midkine in human skin fibrolast." Arch. Dermatol. Res. 289:429–433.
Tajima, S. et al. (1995) Seikagaku 67(7): 938.
Yasuhara, O. et al. (1993) "Midkine, A Novel Neurotrophic Factor, Is Present In Senile Plaques of Alzheimer Disease." Biochem. Biophys. Res. Commun. 192(1): 246–251.

*Primary Examiner*—David L. Fitzgerald
*Attorney, Agent, or Firm*—Saliwanchik, Lloyd & Saliwanchik

[57] ABSTRACT

An anti-ulcer composition is provided, which comprises as an active ingredient at least one of MK protein, its derivative having biological activity of MK protein, and their fragment having biological activity of MK protein, and a pharmaceutically acceptable carrier. The composition exhibits an effect for treating ulcer by promoting autotherapy without recurrence of ulcer.

6 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 432 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (xi) SEQUENCE DESCRIPTION: SEQ ID NO:1:

```
ATGCAGCACC GAGGCTTCCT CCTCCTCACC CTCCTCGCCC TGCTGGCGCT CACCTCCGCG      60

GTCGCCAAAA AGAAAGATAA GGTGAAGAAG GGCGGCCCGG GGAGCGAGTG CGCTGAGTGG     120

GCCTGGGGGC CCTGCACCCC CAGCAGCAAG GATTGCGGCG TGGGTTTCCG CGAGGGCACC     180

TGCGGGGCCC AGACCCAGCG CATCCGGTGC AGGGTGCCCT GCAACTGGAA GAAGGAGTTT     240

GGAGCCGACT GCAAGTACAA GTTTGAGAAC TGGGGTGCGT GTGATGGGGG CACAGGCACC     300

AAAGTCCGCC AAGGCACCCT GAAGAAGGCG CGCTACAATG CTCAGTGCCA GGAGACCATC     360

CGCGTCACCA AGCCCTGCAC CCCCAAGACC AAAGCAAAGG CCAAAGCCAA GAAAGGGAAG     420

GGAAAGGACT AG                                                        432
```

(2) INFORMATION FOR SEQ ID NO:2:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:2:

```
Met Gln His Arg Gly Phe Leu Leu Thr Leu Leu Ala Leu Leu Ala
1               5                   10                  15

Leu Thr Ser Ala Val Ala Lys Lys Asp Lys Val Lys Lys Gly Gly
            20                  25                  30

Pro Gly Ser Glu Cys Ala Glu Trp Ala Trp Gly Pro Cys Thr Pro
            35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
                100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
            130                 135                 140
```

(2) INFORMATION FOR SEQ ID NO:3:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens (xi) SEQUENCE DESCRIPTION: SEQ ID NO:3:

```
Lys Lys Lys Asp Lys Val Lys Lys Gly Gly Pro Gly Ser Glu Cys Ala
1               5                   10                  15

Glu Trp Ala Trp Gly Pro Cys Thr Pro Ser Ser Lys Asp Cys Gly Val
            20                  25                  30

Gly Phe Arg Glu Gly Thr Cys Gly Ala Gln Thr Gln Arg Ile Arg Cys
            35                  40                  45

Arg Val Pro Cys Asn Trp Lys Lys Glu Phe Gly Ala Asp Cys Lys Tyr
    50                  55                  60

Lys Phe Glu Asn Trp Gly Ala Cys Asp Gly Gly Thr Gly Thr Lys Val
65                  70                  75                  80

Arg Gln Gly Thr Leu Lys Lys Ala Arg Tyr Asn Ala Gln Cys Gln Glu
                85                  90                  95

Thr Ile Arg Val Thr Lys Pro Cys Thr Pro Lys Thr Lys Ala Lys Ala
                100                 105                 110

Lys Ala Lys Lys Gly Lys Gly Lys Asp
            115                 120
```

(2) INFORMATION FOR SEQ ID NO:4:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (vi) ORIGINAL SOURCE:
    (A) ORGANISM: mouse (xi) SEQUENCE DESCRIPTION: SEQ ID NO:4:

Lys Lys Lys Glu Lys Val Lys Lys Gly Ser Glu Cys Ser Glu Trp Thr
1               5                   10                  15

Trp Gly Pro Cys Thr Pro Ser Ser Lys Asp Cys Gly Met Gly Phe Arg
            20                  25                  30

Glu Gly Thr Cys Gly Ala Gln Thr Gln Arg Val His Cys Lys Val Pro
            35                  40                  45

Cys Asn Trp Lys Lys Glu Phe Gly Ala Asp Cys Lys Tyr Lys Phe Glu
        50                  55                  60

Ser Trp Gly Ala Cys Asp Gly Ser Thr Gly Thr Lys Ala Arg Gln Gly
65                  70                  75                  80

Thr Leu Lys Lys Ala Arg Tyr Asn Ala Gln Cys Gln Glu Thr Ile Arg
                85                  90                  95

Val Thr Lys Pro Cys Thr Ser Lys Thr Lys Ser Lys Thr Lys Ala Lys
            100                 105                 110

Lys Gly Lys Gly Lys Asp
        115

(2) INFORMATION FOR SEQ ID NO:5:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Homo sapiens (xi) SEQUENCE DESCRIPTION: SEQ ID NO:5:

Cys Lys Tyr Lys Phe Glu Asn Trp Gly Ala Cys Asp Gly Gly Thr Gly
1               5                   10                  15

Thr Lys Val Arg Gln Gly Thr Leu Lys Lys Ala Arg Tyr Asn Ala Gln
            20                  25                  30

Cys Gln Glu Thr Ile Arg Val Thr Lys Pro Cys
        35                  40

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Other nucleic acid
            synthetic DNA (xi) SEQUENCE DESCRIPTION: SEQ ID NO:6:

GCGGAATTCA TGCAGCACCG AGGCTTCCTC                                    30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single -continued

```
    (D) TOPOLOGY: linear (ii) MOLECULE TYPE: Other nucleic acid
        synthetic DNA (xi) SEQUENCE DESCRIPTION: SEQ ID NO:7:

GCGGAATTCC TAGTCCTTTC CCTTCCCTTT                                   30
```

TREATMENT OF PEPTIC ULCERS USING MIDKINE (MK) PROTEINS

FIELD OF THE INVENTION

This invention relates to an anti-ulcer composition comprising as an active ingredient at least one of MK protein, its derivative having biological activity of MK protein, and their fragment having biological activity of MK protein, and a pharmaceutically acceptable carrier.

BACKGROUND OF THE INVENTION

It is presumed that the pathogenesis of peptic ulcer (mainly stomach and duodenal ulcers) results from the impairment of mucosa of the digestive tract by an imbalance between aggressive factors and defense factors. According to this presumption, even though the aggressive factors such as hydrochloric acid or pepsin are increased, the defense factors such as mucous or blood stream are also increased in the normal conditions so that mucosal tissues are not injured, thereby maintaining the homeostasis which gastric mucosa essentially possesses. When the balance is disrupted, the gastric mucosa is impaired and can result in ulcer.

Based on this mechanism, a number of anti-ulcer drugs have been developed and clinically used. For example, histamine H2 receptor blockers, which suppress gastric acid secretion, and proton pump inhibitors have been launched on the market and the results of treating ulcer have greatly progressed. Sucrose aluminum sulfate, which protects the injured mucosa and enhances the healing of ulcer though it does not inhibit gastric acid secretion has also been developed. It enjoys acceptance equivalent to that of H2 blockers. In addition, pharmaceutical compositions for treating peptic ulcer containing acid resistant fibroblast growth factor (FGF) (JP-WA-Hei 7-505736), a prophylactic and therapeutic composition for gastric mucosal disorders containing epidermal growth factor (EGF) (JP-WA-Hei 7-503471), and the like, are also under development. These growth factors were developed initially as therapeutics for treating wounds. Based on their biological activities, these factors are also being investigated for use as anti-ulcer drugs.

Recently, a new growth factor was found which is entirely different in structure from a variety of known heparin-binding growth factors. Kadomatsu et al. cloned cDNA complementary to mRNA from mouse embryonic tumor cells in which expression of mRNA was transiently enhanced at the initial stage of differentiation and induction by treatment with retinoic acid. The factor isolated was named MK 1 (Kadomatsu et al. [1988] Biochem. Biophys. Res. Commun. 151:1312–1318). The protein (hereinafter referred to as MK protein, MK polypeptide or simply MK) encoded by MK 1 cDNA is a novel protein rich in basic amino acids and cysteines and does not exhibit substantial homology to any other known proteins. Subsequently, analysis of the cDNA clone derived from mouse embryonic tumor cells indicated that there were three types of clones which had different structures at the 5' non-translational regions, but possessed an identical coding region. These three types were identified as the clones MK 1, MK 2, and MK 3. Among these clones, MK 2 was found to have the structure corresponding to the dominant mRNAs (Tomomura, M. et al. [1990] J. Biol Chem. 265:10765–10770).

Human MK cDNA has been cloned from human MK gene library using mouse MK 2 cDNA (Tsutsui, J. et al. [1991] Biochem. Biophys. Res. Commun. 176:792–797; U.S. Pat. No. 5,210,026). Sequencing revealed that human MK and mouse MK have 87% homology in their amino acid sequence.

MK protein has a molecular weight of 13 kDa and consists of 121 amino acid residues in human and 118 residues in mouse, both of which are rich in basic amino acids and cysteines. MK has some biological activities such as abilities to grow neurite, to maintain neurocytes alive, and to stimulate the fibrinolytic system in vascular endothelial cells. The MK molecule has two domains (½ molecule of the N-terminal and ½ molecule of the C-terminal domains) which are formed by the disulfide bond within the molecule. The biological activities are attributable to the C-terminal domain (Muramatsu, H. et al. [1995] Biochem. Biophys. Res. Commun. 206:468–473).

In late 1990, "heparin binding growth associated molecule" (HB-GAM), which has an amino acid sequence highly homologous to MK, was reported (Mercenmies, T. and Rauvala, H. [1990] J. Biol. Chem. 265:16721–16724). HB-GAM is also called pleiotrophin (PTN) (Li, Y. S. et al. [1990] Science 250:1690–1694), OSF-1 (Tezuka, K. et al. [1990] Biochem. Biophys. Res. Commun. 173:246–251), or heparin binding neurotrophic factor (HBNF) (Kovesde, I. et al. [1990] Biochem. Biophys. Res. Commun. 172:850–854).

HB-GAM is a protein with the molecular weight of 15 KDa and has an ability to stimulate the growth of neurites (Rauvala, H. [1989] EMBO J. 8:2933–2941). The structure of this protein is so highly preserved among species as to differ in only one amino acid between human and mouse (Li, Y. -S., et al. [1990] Science 250:1690–1694). HB-GAM has 50% homology to human MK. The positions of all cysteines are preserved in both proteins (Mercenmies, T. and Rauvala, H. [1990] J. Biol. Chem. 265:16721–16724; Li, Y. -S., et al. [1990] Science 250:1690–1694) as is the disulfide bond (Fabri, L. et al. [1992] Biochem. Int. 28:1–9). Particularly, MK and HB-GAM are highly homologous in the two domains surrounding the S-S bond. These results indicate that MK and HB-GAM form a new family as heparin binding growth factors (Muramatsu, T. et al. [1994] Dev. Growth Differ. 36:1–8).

It has also been reported that the expression level of MK increased in a variety of human cancers (Tsutsui, J. et al. [1993] Cancer Res. 53:1281–1285). In all six cases of Wilms' tumor, MK was found not to be expressed. In the patients with liver or esophagus cancer, MK was not expressed in noncancerous areas but was often highly expressed in cancerous areas. In cases of colon and stomach cancers, the expression of MK was observed often even in the noncancerous areas, but strong expression mostly occurred in the cancerous areas. MK was also expressed in lung cancer, breast cancer, and neuroblastoma. Thus, the increase in the MK expression level is considered to correlate with the progress of cancer.

It was also reported that, in experimental cerebral infarction in rats, MK was expressed around the area of infarction and also appeared in the edematic area that recovered later without proceeding to necrosis at such an early stage as one day after the onset of infarction (Yoshida, Y. et al. [1995] Dev. Brain Res. 85:25–30). These results suggest that MK plays a very important role not only in the process of embryonic development but also in the repair of tissues. A disorder of the retina caused by continuous light irradiation was found to be ameliorated by the injection of MK (Unoki, K. et al. [1994] Inv. Ophthal. Vis. Sci. 35:4603–4068).

Furthermore, in the brain of patients with Alzheimer's disease, MK was detected in the senile plaques without exception (Yasuhara, O. et al. [1993] *Biochem. Biophys. Res. Commun.* 192:246–251). A recent report demonstrated that, as a result of treating cultured normal human skin fibroblasts with a variety of concentrations of MK, a treatment at 60 ng/ml for 72 hours enhanced synthesis of collagen and mucopolysaccharide to twice the normal level (Tajima, S. et al. [1995] *Seikagaku* 67(7):938; Yamada, H. et al. [1997] *Arch. Dermatol. Res.* 289:429–433).

There are many anti-ulcer drugs which inhibit acid secretion or increase defense factors, but no drug has been developed yet which can achieve an ultimate object of anti-ulcer drugs, which is to completely cure ulcers without causing recurrence.

It can be said that currently used H2 blockers and proton pump inhibitors are, in terms of a cure, dependent upon autotherapy due to a natural increase of the cells. Under such circumstances, the growth factors such as EGF and FGF have been launched to aim at curing the ulcer nearly to the previous level by enhancing the growth of cells at ulcerous regions.

The in vivo mechanism of these factors for the healing of ulcer is as follows. First, fibroblasts proliferate by the action of EGF, FGF, etc. at ulcerous regions with the simultaneous occurrence of angiogenesis by the action of FGF and the like, followed by granulation. Then, TGF-α, EGF, etc. cause migration and growth of epithelial cells, accompanied by disappearance of granulation. Thus, the ulcerous regions recover to the normal conditions.

Since this healing mechanism usually involves substances that the living body inherently possesses, no particular problem is expected to occur. However, when EGF and FGF are forcibly given, there is a possibility that undesirable effects take place. For example, when EGF is administered, only epithelial cells are healed without enough granulation. In the case of administration of FGF, excessive granulation may possibly be induced, thereby failing to heal to the normal state but possibly causing recurrence of ulcer.

BRIEF SUMMARY OF THE INVENTION

An object of the present invention is to provide an anti-ulcer drug based on a new mechanism that promotes autotherapy without causing recurrence of ulcer.

MK is a secreted protein with low molecular weight, rich in basic amino acids and cysteines, and functions as a growth and differentiation factor, but its structure is entirely different from those of known growth factors. It also has such properties that: it keeps cells alive; it is stable against acid; it repairs the disorder in the retina that may possibly be produced by active oxygen; and it is produced by induction with retinoic acid which is a precursor of vitamin A. Thus, it is considered that MK is involved in regeneration of mucosal cells. These facts suggest that MK and its derivatives can be used as a new anti-ulcer drug for preventing or treating various ulcerative diseases based on the mechanism different from that of the existing growth factors. As a result of intensive investigation, the present inventors have found that the above object can be achieved by using MK protein.

Namely, the present invention relates to an anti-ulcer composition comprising as an active ingredient at least one of MK protein, its derivative having biological activity of MK protein, and their fragment having biological activity of MK protein, and a pharmaceutically acceptable carrier.

The present invention also relates to the anti-ulcer composition as described above, wherein at least one of said MK protein, its derivative, and their fragment is in the form of a pharmaceutically acceptable salt.

Further, the present invention relates to a method of treating ulcer, which comprises administering to a patient the anti-ulcer composition as described above.

DETAILED DISCLOSURE OF THE INVENTION

MK protein used in the present invention includes MK protein isolated from nature, especially MK protein derived from human and mammals, and genetically produced recombinant MK protein. Particularly preferred is recombinant human MK protein. Recombinant MK proteins included within the scope of the present invention are polypeptides that are different in the length of amino acid sequence (for example, MK polypeptide shown as SEQ ID NO: 5). MK protein has a signal peptide at its N-terminal region. Such a polypeptide as a whole and a part thereof are also within the scope of the present invention.

Derivatives of MK protein that fall within the scope of the present invention include proteins or polypeptides which are slightly different in the number of amino acids and/or the amino acid sequence from natural MK protein, without substantial changes of the biological activities of MK protein. These derivatives include those deficient in a part of the amino acid sequence of natural MK protein, those in which amino acid(s) of natural MK protein are partially replaced with other amino acid(s), those in which other amino acid(s) are introduced or added, and those with different lengths of amino acid sequence. Amino acid residue(s) to be substituted or introduced are not restricted to the natural form, but may be a modified or non-natural form.

According to the present invention, MK protein, its derivatives having the biological activity of MK protein, and their fragments having the biological activity of MK protein may be in the form of pharmaceutically acceptable salts. The pharmaceutically acceptable salts used herein means, while keeping the desirable biological activity of MK protein, those free from any new undesirable toxicity. Examples of such salts include acid-added salts with inorganic acid such as hydrochloric acid, bromic acid, sulfuric acid, phosphoric acid, nitric acid, or the like, acid-added salts with organic acid such as acetic acid, oxalic acid, tartaric acid, succinic acid, maleic acid, fumaric acid, gluconic acid, citric acid, malic acid, ascorbic acid, benzoic acid, tannic acid, or the like, salts with metals such as zinc, calcium bismus, barium, magnesium, aluminum, copper, cobalt, nickel, cadmium, or the like, and salts with organic cations produced from N,N'-dibenzylethylenediamine or ethylenediamine.

MK protein according to the present invention can be prepared by either recombinant DNA techniques, chemical synthesis, or other means known in the art. In the case of using recombinant DNA techniques, it is important to select an appropriate expression vector-host system in order to obtain a large amount of MK protein. Currently, a variety of proteins are produced using as a host microorganisms such as *Escherichia coli* or *Bacillus subtilis* and eucaryotic cells such as yeast, insects, or mammals, which are transformed with an expression vector carrying a foreign gene. A suitable example of the expression system used in this invention includes an expression vector containing the promoter and the terminator of the alcohol oxidase gene derived from the chromosome of yeast *Pichia pastoris* (Pichia yeast) and, as a host, methanol-dependent Pichia yeast (JP-A-Hei 8-228779).

The developments in technology have made it possible to freely modify proteins by site-directed mutagenesis that had been enabled by the establishment of DNA chemical synthesis and its automation, and to produce such proteins in a large amount using microorganisms. Further, a system of precise peptide chemistry enables chemical synthesis not only of complex peptides but also proteins. By means of these technologies, one skilled in the art can readily produce MK protein derivatives having the biological activity of MK protein based on the known structure and active domain of MK protein and using the known assay system of its biological activity (Muramatsu, H. et al. [1993] Developmental Biology 159:392–402; Kojima, S. et al. [1995] J. Biol. Chem. 270:9590–9596).

When MK protein is to be secreted into a culture medium, the protein can be recovered from the culture supernatant of directly from the host cells, depending on the expression method in the host. Its purification can be carried out in accordance with the method of Muramatsu et al. (Muramatsu, H. et al. [1991] Biochem. Biophys. Res. Commun. 177:652–658).

The mature MK protein thus obtained is exemplified by MK protein with the amino acid sequence shown in SEQ ID NO: 3 (human origin) and SEQ ID NO: 4 (mouse origin).

Mature human MK protein shown in the SEQ ID NO: 3 exhibited, as indicated in Table 1, a significant ($p<0.05$) effect for promoting cure of acetic acid-induced ulcers, which were experimentally prepared in rat stomach as a pathological model of the chronic gastric ulcer. Thus, growth and differentiation factor MK protein was found to have anti-ulcer activity. From the biological activity of MK protein, it would exhibit anti-ulcer effect to promote autotherapy due to a new mechanism of action.

The anti-ulcer composition of the present invention can be given either orally or parenterally. Preferably, the compositions are administered orally. The formulation for oral administration includes, for example, tablets, granules, capsules, syrup, troches, and the like. The formulation for parenteral administration includes, for example, injection, preparations for administration per rectum, eye drops, preparations for percutaneous administration, and the like. Such formulations can be prepared together with generally used pharmaceutically acceptable carriers such as an excipient, a binder, a disintegrating agent, a lubricant, a solubilizing agent, and the like. The active ingredient is contained in the anti-ulcer composition in an amount effective for treating ulcer. One skilled in the art would readily determine such an amount of the active ingredient.

In the case of peptic ulcerative disorders, the daily dose for oral administration of MK polypeptide or its homologues ranges from about 0.01 μg/kg body weight to about 30 mg/kg body weight, preferably about 0.1 μg/kg body weight to about 10 mg/kg body weight. Peptic ulcerative disorders used herein include ulcerative esophagitis, duodenal ulcer, gastric ulcer, duodinitis, inflammatory enteric disorders, ulcerative colitis, and erosion of peptic mucosa and its similar disorders.

Use of the anti-ulcer composition according to the present invention in combination with currently used anti-ulcer drugs (for example, histamine H2 blocker, cimethidine, etc.) can elevate the anti-ulcer effects. Also, judging from the biological activity of MK, a synergistic effect can be expected by using the anti-ulcer composition of the present invention together with heparin.

The following examples will demonstrate the present invention in more detail but are not to be construed to limit the scope of the invention.

EXAMPLE 1

Production of Recombinant Human MK Protein

Human MK cDNA was prepared from the cultured cell line G401 derived from Wilm's tumor by the standard method (Tsutsui, J. et al. [1991] Biochem. Biophys. Res. Commun. 176:792–797). A sense PCR primer containing EcoRI recognition site: 5'-GCGGAATTCATG-CAGCACCGAGGCTTCCTC-3' (SEQ ID NO: 6) and an antisense PCR primer: 5'-GCGGAATTCCTAGTCC-TTTCCCTTCCCTTT-3' (SEQ ID NO: 7) were synthesized and human MK cDNA was prepared by the PCR method using the above primer set and the mRNA as a template. In this case, each primer was designed to contain EcoRI recognition sites (5'-GAATTC-3') so as to insert the EcoRI recognition site into both ends of human MK cDNA. PCR was carried out by repeating a cycle of 93° C., 37° C., and 72° C. 30 times. Using MK cDNA thus obtained, human MK protein (containing EcoRI sites at both ends) was produced in accordance with the method described in JP-A-Hei 8-228779.

MK cDNA and expression vector pHIL301 (JP-A-Hei 8-228779) for yeast Pichia pastoris GS 115 (hereinafter referred to as Pichia yeast GS 115 or simply GS 115) were digested with the restriction enzyme EcoRI, and both were ligated using the ligation kit (Takara Shuzo).

Then, the recombinant expression vector prepared as described above was used to transform Pichia yeast GS 115 by electroporation. Pichia yeast GS 115 has neither histidine productivity nor the resistance to neomycin, while the expression vector pHIL301 has the histidine gene and the neomycin resistant gene. Thus, it is possible to obtain desired transformants with MK gene by culturing GS 115 in the medium containing no histidine but G418.

According to the method described above, plural clones were obtained and the resulting clones were examined in a small scale by Western-blot as to whether the clones secret MK when cultured under induction with methanol. Western-blot analysis was carried out using rabbit antimouse MK polyclonal antibody.

One of the clones that secreted MK into the culture supernatant under induction was named T3L-50-4P and was cultured according to the method described in JP-A-Hei 8-228779. Secreted MK was recovered from the culture supernatant and purified by ion exchange chromatography and affinity chromatography using a heparin column to obtain MK with a high purity. The base sequence of human MK DNA that was cloned in this Example is shown in SEQ ID NO: 1. Human MK cDNA of SEQ ID NO: 1 encodes 143 amino acid residues from Met (ATG 1–3) to Asp (GAC, 427–429) (SEQ ID NO: 2), which consists of the signal peptide with 22 amino acid residues from Met (ATG 1–3) to Ala (GCC, 64–66) and the subsequent mature protein with 121 amino acid residues from the Lys (AAA, 67–69) to Asp (GAC, 427–429).

EXAMPLE 2

Healing Effects of MK on Chronic Gastric Ulcer

The healing effects of mature human MK protein that was obtained in Example 1 (SEQ ID NO: 3) on acetic acid-induced ulcer in rats were examined as follows. Six-week-old Slc:SD male rats were purchased and preliminarily fed for one week placing two rats per cage. After the preliminary feeding, abdomen of rats were opened under anesthesia with pentobarbital (35 mg/kg) and 0.3 ml of glacial acetic acid was poured on the boundary between corpus ventriculi of anterior wall of stomach and pyloric part of stomach so that the surface of tunica serosa ventricle was contacted with glacial acetic acid for one minute to cause ulcer.

From the fifth day after ulcer was formed, the rats were orally given twice daily for consecutive 12 days the test drugs with the doses shown in Table 1 (MK 1 μg/5ml saline or MK 100 μg/5 ml saline). On the 13th day after the initiation of administration of the drugs, the rats were killed by vertebral cervical dislocation. After ligation of cardiac part of stomach and pyloric part of stomach, the stomach was taken out, into which 10 ml of saline was poured. The outside of the stomach was weakly fixed with 5% formalin and then the stomach was cut along curvatura ventriculi major. Long and short axes of the ulcer were measured and their multiplied value was taken as "ulcer index" of the size of ulcer. The results are shown in Table 1. It is evident that 1 μg/kg of MK exhibits the significant effects for promoting cure of the ulcer.

TABLE 1

Effects of MK for curing acetic acid-induced ulcer in rat

| Group | Dose | Number of rats | Ulcer index | Cure-promoting effect (%) |
|---|---|---|---|---|
| Control | — | 10 | 9.8 ± 1.5 | — |
| MK | 1 μg/kg | 10 | 3.7 ± 0.9* | 62.2 |
| MK | 100 μg/kg | 10 | 6.7 ± 1.5 | 31.5 |

*Significant difference ($p < 0.05$) according to Dunnet's multiple comparison test as compared with control. The value is mean ± S.E.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of treating peptic ulcer which comprises administering to a patient an effective amount of an anti-ulcer composition comprising as an active ingredient at least one of MK protein, or a derivative or fragment thereof having biological activity of said MK protein, and a pharmaceutically acceptable carrier.

2. The method of treating ulcer according to claim 1, wherein said MK protein, or said derivative or fragment thereof, comprises an amino acid sequence selected from the group consisting of SEQ ID NO. 2, SEQ ID NO. 3, and SEQ ID NO. 4.

3. The method of treating ulcer according to claim 1, wherein at least one of said MK protein, derivative, or fragment is in the form of a pharmaceutically acceptable salt.

4. The method of treating ulcer according to claim 1, wherein said peptic ulcer is gastric ulcer.

5. The method of treating ulcer according to claim 1, further comprising administering to said patient an effective amount of an additional anti-ulcer drug.

6. The method of treating ulcer according to claim 5, wherein said additional anti-ulcer drug is selected from the group consisting of histamine H-2 blockers, cimethidine, proton pump inhibitors, and heparin.

* * * * *

UNITED STATES PATENT AND TRADEMARK OFFICE
CERTIFICATE OF CORRECTION

PATENT NO. : 6,083,907
DATED : July 4, 2000
INVENTOR(S) : Masayuki Uchida, et al.

It is certified that error appears in the above-identified patent and that said Letters Patent is hereby corrected as shown below:

Column 6, line 17: "93°C., 37°C.," should read --93°C, 37°C,--.

Column 6, line 17: "72°C." should read --72°C--.

Column 6, line 23: "GS 115" should read --GS115--.

Column 6, line 24: "GS 115 or simply GS 115" should read --GS115 or simply GS115--.

Column 6, line 28: "GS 115" should read --GS115--.

Column 6, line 29: "GS 115" should read --GS115--.

Column 6, line 33: "GS 115" should read --GS115--.

Signed and Sealed this

Eighth Day of May, 2001

Attest:

NICHOLAS P. GODICI

Attesting Officer

Acting Director of the United States Patent and Trademark Office